US009314336B2

(12) United States Patent
Furnish et al.

(10) Patent No.: US 9,314,336 B2
(45) Date of Patent: Apr. 19, 2016

(54) ADJUSTMENT ASSEMBLY FOR AN ADJUSTABLE PROSTHETIC VALVE DEVICE (75) Inventors: Gregory R. Furnish, Louisville, KY (US); Brian K. Wells, La Grange, KY (US); Christopher Bethards, Louisville, KY (US); Bruce R. Weir, Plymouth, MN (US); Melinda K. Kovach, Plymouth, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 444 days.

(21) Appl. No.: 13/982,535

(22) PCT Filed: Jan. 31, 2012

(86) PCT No.: PCT/US2012/023333
§ 371 (c)(1),
(2), (4) Date: Nov. 18, 2013

(87) PCT Pub. No.: WO2012/106344
PCT Pub. Date: Aug. 9, 2012

(65) Prior Publication Data
US 2014/0067055 A1 Mar. 6, 2014

Related U.S. Application Data (60) Provisional application No. 61/438,129, filed on Jan. 31, 2011, provisional application No. 61/569,571, filed on Dec. 12, 2011.

(51) Int. Cl.
*A61F 2/24* (2006.01)
*A61F 2/00* (2006.01)

(52) U.S. Cl.
CPC .............. *A61F 2/2466* (2013.01); *A61F 2/2445* (2013.01); *A61F 2/0036* (2013.01); *A61F 2/2448* (2013.01); *A61F 2250/001* (2013.01); *A61F 2250/0007* (2013.01)

(58) Field of Classification Search
CPC ....... A61F 2/24; A61F 2/2466; A61F 2/2425; A61F 2/2448
USPC .................................................. 623/2.1–2.39
See application file for complete search history.

(56) References Cited

U.S. PATENT DOCUMENTS 7,175,660 B2 * 2/2007 Cartledge ........ A61B 17/00234
606/139
7,442,207 B2 * 10/2008 Rafiee .............. A61B 17/00234
623/2.37

(Continued)

FOREIGN PATENT DOCUMENTS

DE 202005013648 U1 3/2006
WO 0149245 A2 7/2001

(Continued)

OTHER PUBLICATIONS

International Search Report and Written Opinion for Application No. PCT/US2012/023359 dated May 11, 2013.

(Continued)

*Primary Examiner* — Suzette J Gherbi
(74) *Attorney, Agent, or Firm* — Lerner, David, Littenberg, Krumholz & Mentlik, LLP (57) ABSTRACT An adjustment assembly for an adjustable prosthetic valve device includes a gearbox housing formed from two gearbox shells coupled to one another and held together by two gearbox sleeves each having an internal cavity adapted to accommodate respective lateral portions of the gearbox shells when the gearbox shells are coupled to one another. A gear assembly, including a center gear and two driven gears, is supported within the gearbox housing. Gear teeth of each of the driven gears engage gear teeth of the center gear such that rotation of the center gear causes rotation of the driven gears. At least one of the driven gears is adapted to engage a transmission mechanism that transmits the rotation thereof to another part of the adjustable prosthetic valve device to accomplish an adjustment to the size and/or shape of the adjustable prosthetic valve device.

23 Claims, 9 Drawing Sheets

(56) References Cited

U.S. PATENT DOCUMENTS

| | | | |
|---|---|---|---|
| 7,455,690 B2 * | 11/2008 | Cartledge | A61B 17/00234 600/30 |
| 8,574,289 B2 * | 11/2013 | Cartledge | A61B 17/0401 604/96.01 |
| 8,758,372 B2 * | 6/2014 | Cartledge | A61B 5/061 606/151 |
| 8,778,021 B2 * | 7/2014 | Cartledge | A61B 17/12 623/2.11 |
| 9,107,750 B2 * | 8/2015 | Cartledge | A61B 17/068 |
| 9,138,316 B2 * | 9/2015 | Bielefeld | A61F 2/2466 |
| 2001/0049558 A1 | 12/2001 | Liddicoat et al. | |
| 2003/0191416 A1 | 10/2003 | Rosenman et al. | |
| 2005/0222665 A1 | 10/2005 | Aranyi | |
| 2005/0222678 A1 * | 10/2005 | Lashinski | A61F 2/2451 623/2.11 |
| 2006/0241748 A1 * | 10/2006 | Lee | A61F 2/2445 623/2.37 |
| 2008/0033545 A1 | 2/2008 | Bergin | |
| 2008/0308600 A1 | 12/2008 | Kana | |
| 2009/0125102 A1 * | 5/2009 | Cartledge | A61B 17/00234 623/2.11 |
| 2009/0192605 A1 | 7/2009 | Gloss et al. | |
| 2009/0266367 A1 | 10/2009 | Ziv et al. | |
| 2010/0010538 A1 | 1/2010 | Juravic et al. | |
| 2010/0161047 A1 | 6/2010 | Cabiri | |
| 2010/0211166 A1 * | 8/2010 | Miller | A61F 2/2448 623/2.37 |
| 2011/0000347 A1 | 1/2011 | Stark | |
| 2011/0015617 A1 | 1/2011 | Chesnin et al. | |
| 2011/0066231 A1 | 3/2011 | Cartledge et al. | |
| 2011/0190879 A1 * | 8/2011 | Bobo | A61F 2/2445 623/2.37 |
| 2011/0202130 A1 * | 8/2011 | Cartledge | A61F 2/2445 623/2.37 |
| 2012/0136436 A1 | 5/2012 | Cabiri et al. | |

FOREIGN PATENT DOCUMENTS

| | | |
|---|---|---|
| WO | 2008/085814 A2 | 7/2008 |
| WO | 2009126629 A1 | 10/2009 |
| WO | 2010014671 A1 | 2/2010 |
| WO | 2010073246 A2 | 7/2010 |

OTHER PUBLICATIONS

International Search Report for Application No. PCT/US2012/023309 dated Jun. 20, 2012.

International Search Report for Application No. PCT/US2012/023340 dated Jun. 4, 2012.

International Search Report for Application No. PCT/US2012/023333 dated May 10, 2012.

International Search Report for Application No. PCT/US/2012/023349 dated Jun. 18, 2012.

* cited by examiner

ADJUSTMENT ASSEMBLY FOR AN ADJUSTABLE PROSTHETIC VALVE DEVICE

CROSS-REFERENCE TO RELATED APPLICATION

The present application claims the benefit of the filing dates of U.S. Provisional Patent Application No. 61/438,129 filed Jan. 31, 2011 and of U.S. Provisional Patent Application No. 61/569,571 filed Dec. 12, 2011, the entire disclosures of which are each hereby incorporated herein by reference.

BACKGROUND OF THE INVENTION

The present invention broadly relates generally to an adjustable prosthetic anatomical device for adjusting the size and/or shape of an anatomic orifice or lumen. More particularly, the present invention relates to an adjustment assembly for an adjustable annuloplasty ring for repairing a valve such as a mitral valve in a human patient.

Heart valve disease is a condition in which one or more valves of the heart fail to function properly. Diseased heart valves may be categorized as either stenotic, wherein the valve does not open sufficiently to allow adequate forward flow of blood through the valve, or incompetent, wherein the valve does not close completely causing excessive backward flow of blood through the valve when the valve is closed.

By way of one specific example, the mitral valve is the inflow valve for the left side of the heart. Blood flows from the lungs, where it picks up oxygen, through the pulmonary veins, to the left atrium of the heart. After the left atrium fills with blood, the mitral valve allows blood to flow from the left atrium into the heart's main pumping chamber called the left ventricle. It then closes to keep blood from leaking back into the left atrium or lungs when the left ventricle contracts to push blood out to the body.

Valve disease relating to the mitral valve often involves secondary mitral regurgitation which is the backward flow of blood from the left ventricle to the left atrium resulting from imperfections in the mitral valve. One repair technique for treating regurgitation is called annuloplasty, in which the size and/or shape of the valve annulus is modified by securing a prosthetic adjustable annuloplasty ring to an interior wall of the heart around the valve annulus. The size and/or shape of the annuloplasty ring is adjusted in situ for maintaining coaptation to prevent reversed blood flow.

Examples of an adjustable annuloplasty ring are disclosed in United States Patent Application Publication No. 2011/0066231, the entire disclosure of which is incorporated herein by reference. The disclosed annuloplasty ring includes an adjustment assembly for expanding or contracting the size and/or shape of the ring and of the opening formed by the ring.

BRIEF SUMMARY OF THE INVENTION

The present invention broadly relates generally to an adjustable prosthetic valve device for adjusting the size and/or shape of an anatomic orifice or lumen, and more particularly to an adjustment assembly for use in an adjustable prosthetic valve device.

According to one embodiment, an adjustment assembly for an adjustable prosthetic valve device includes a first gearbox sleeve and a second gearbox sleeve, each gearbox sleeve forming an internal cavity therein, the first and second gearbox sleeves each having at least one opening adjacent a first end thereof. The adjustment assembly also includes a gearbox housing comprising a first gearbox shell and a second gearbox shell adapted to at least partially interlock with one another. The first and second gearbox shells each comprise a center portion having an opening therein, each gearbox shell having a first lateral portion and a second lateral portion. At least one of the first and second lateral portions of each gearbox shell has a projection on an exterior surface thereof, each projection adapted to engage a respective opening formed adjacent the first end of one of the gearbox sleeves when the first and second lateral portions are at least partially inserted within the internal cavities of the first and second gearbox sleeves, whereby the first and second gearbox shells are prevented from separating from one another. The adjustment assembly includes a center gear arranged at least partially within the gearbox housing. The center gear comprises a gear portion and a shaft portion, the shaft portion being adapted to engage an adjustment tool inserted through one of the openings in the gearbox housing. The adjustment assembly further includes a first driven gear and a second driven gear each arranged at least partially within the gearbox housing. The first and second driven gears each comprise a gear portion that engages the gear portion of the center gear, and a shaft portion. The shaft portion of the first driven gear extends at least partially within an opening formed by the first lateral portions of the gearbox shells and the shaft portion of the second driven gear extends at least partially within an opening formed by the second lateral portions of the gearbox shells.

In accordance with the above embodiment, at least one of the first gearbox sleeve and the second gearbox sleeve is integrally molded. The gear portion of the center gear and the shaft portion of the center gear are integrally molded with one another. The gear portion and the shaft portion of at least one of the driven gears are integrally molded with one another. The center gear includes a set of internal threads along at least part of a length of a bore formed therein. The center gear includes a hole having a shape adapted to engage an adjustment mechanism of an adjustment tool.

According to another embodiment, an adjustment assembly for an adjustable prosthetic valve device comprises a first gearbox sleeve having a first end and a second end, and forming a cavity therein, a second gearbox sleeve having a first end and a second end, and forming a cavity therein, and a gearbox housing comprising a first gearbox shell and a second gearbox shell. The first and second gearbox shells each comprise a center portion and two lateral portions extending from opposite sides of the center portion. At least one of the lateral portions of each gearbox shell has a projection on an exterior surface thereof. A first end of each gearbox sleeve includes at least one opening adapted to engage a corresponding projection formed on one of the gearbox shells, whereby the gearbox shells are held together to form a gearbox housing. The gearbox housing is adapted to support a gear assembly therein. The gear assembly comprises a center gear and two driven gears, each of the gears comprising a shaft portion and a gear portion. The gear portion of the center gear engages the gear portions of each of the driven gears. An interior surface of each lateral portion of the gearbox shells provides a bearing surface for the shaft portion of a corresponding one of the driven gears. The center portion of each gearbox shell includes an opening adapted to accommodate an end of the shaft portion of the center gear.

In accordance with this embodiment, at least one of the first gearbox sleeve and the second gearbox sleeve is integrally molded. The shaft portion of the center gear and the gear portion of the center gear are integrally molded with one another. The shaft portion and the gear portion of at least one of the driven gears are integrally molded with one another.

The center gear includes a set of internal threads along at least part of a length of a bore formed therein. The center gear includes a hole having a shape adapted to engage an adjustment mechanism of an adjustment tool.

According to a further embodiment, a gearbox sleeve for an adjustable prosthetic valve device comprises a first end forming an internal cavity therein, a second end adapted to engage a spar of the adjustable prosthetic valve device, and at least one opening formed adjacent the first end. The internal cavity is adapted for accommodating portions of at least two gearbox shells therein to hold the at least two gearbox shells together. The at least one opening is adapted to engage a projection formed on an exterior surface of at least one gearbox shell.

In accordance with this embodiment, the gearbox sleeve is integrally molded from a single piece of material.

In a still further embodiment, a gearbox for an adjustable prosthetic valve device comprises a gearbox housing comprising a first gearbox shell and a second gearbox shell adapted to at least partially interlock with one another. The first and second gearbox shells each comprise a center portion having an opening therein. Each gearbox shell has a first lateral portion and a second lateral portion. At least one of the first lateral portion and the second lateral portion of each gearbox shell have a projection on an exterior surface thereof. A center gear is arranged at least partially within the gearbox housing. The center gear comprises a gear portion and a shaft portion, the shaft portion adapted to engage an adjustment tool inserted through one of the openings in the gearbox housing. A first driven gear and a second driven gear are each arranged at least partially within the gearbox housing, the first and second driven gears each comprising a gear portion that engages the gear portion of the center gear and a shaft portion. The shaft portion of the first driven gear extends at least partially within an opening formed by the first lateral portions of the gearbox shells. The shaft portion of the second driven gear extends at least partially within an opening formed by the second lateral portions of the gearbox shells.

In accordance with the above embodiment, the gear portion of the center gear and the shaft portion of the center gear are integrally molded with one another. The gear portion and the shaft portion of at least one of the driven gears are integrally molded with one another. The center gear includes a set of internal threads along at least part of a length of a bore formed therein. The center gear includes a hole having a shape adapted to engage an adjustment mechanism of an adjustment tool.

According to a still further embodiment, a housing for an adjustment assembly for an adjustable prosthetic valve device comprises a first gearbox sleeve and a second gearbox sleeve, each gearbox sleeve forming an internal cavity therein. The first and second gearbox sleeves each have at least one opening adjacent a first end thereof. The housing also includes a gearbox housing comprising a first gearbox shell and a second gearbox shell adapted to at least partially interlock with one another. The first and second gearbox shells each comprise a center portion having an opening therein, each gearbox shell having a first lateral portion and a second lateral portion, wherein at least one of the first and second lateral portions of each gearbox shell has a projection on an exterior surface thereof, each projection adapted to engage a respective opening formed adjacent the first end of one of the gearbox sleeves when the first and second lateral portions are at least partially inserted within the internal cavities of the first and second gearbox sleeves, whereby the first and second gearbox shells are prevented from separating from one another.

In accordance with the above embodiment, at least one of the first gearbox sleeve and the second gearbox sleeve is integrally molded. The gear portion of the center gear and the shaft portion of the center gear are integrally molded with one another.

According to a further embodiment, an adjustment assembly for an adjustable prosthetic valve device is provided as shown and described herein.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents that operate in a similar manner to accomplish a similar purpose.

Figure 1:
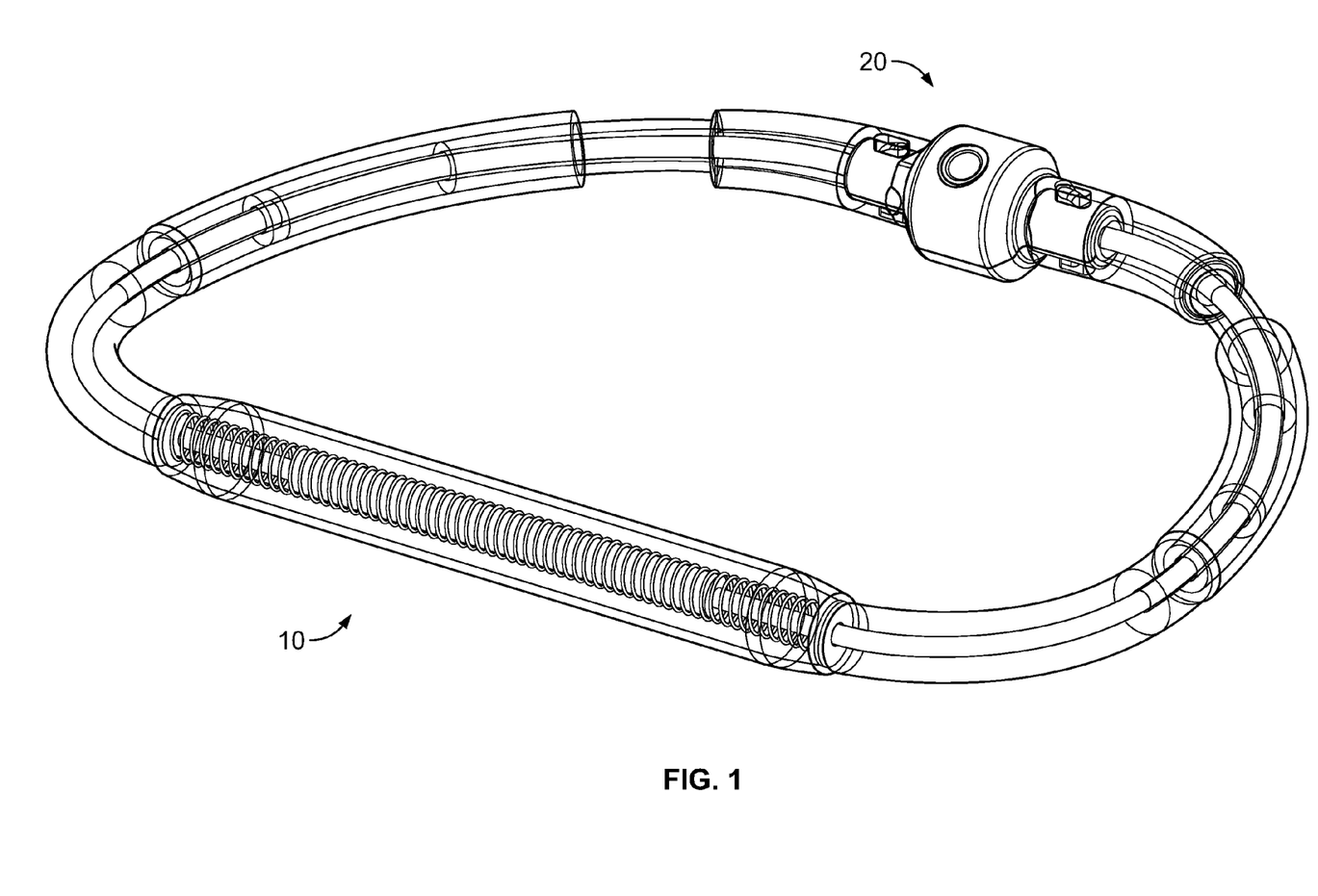
FIG. 1 is a perspective view of an adjustable prosthetic valve device including an adjustment assembly according to an embodiment of the present invention.

FIG. 1 shows a perspective view of an adjustable prosthetic anatomical device 10, for example, an adjustable annuloplasty ring, which includes an adjustment assembly 20 according to an exemplary embodiment of the present invention.

Figure 2A:
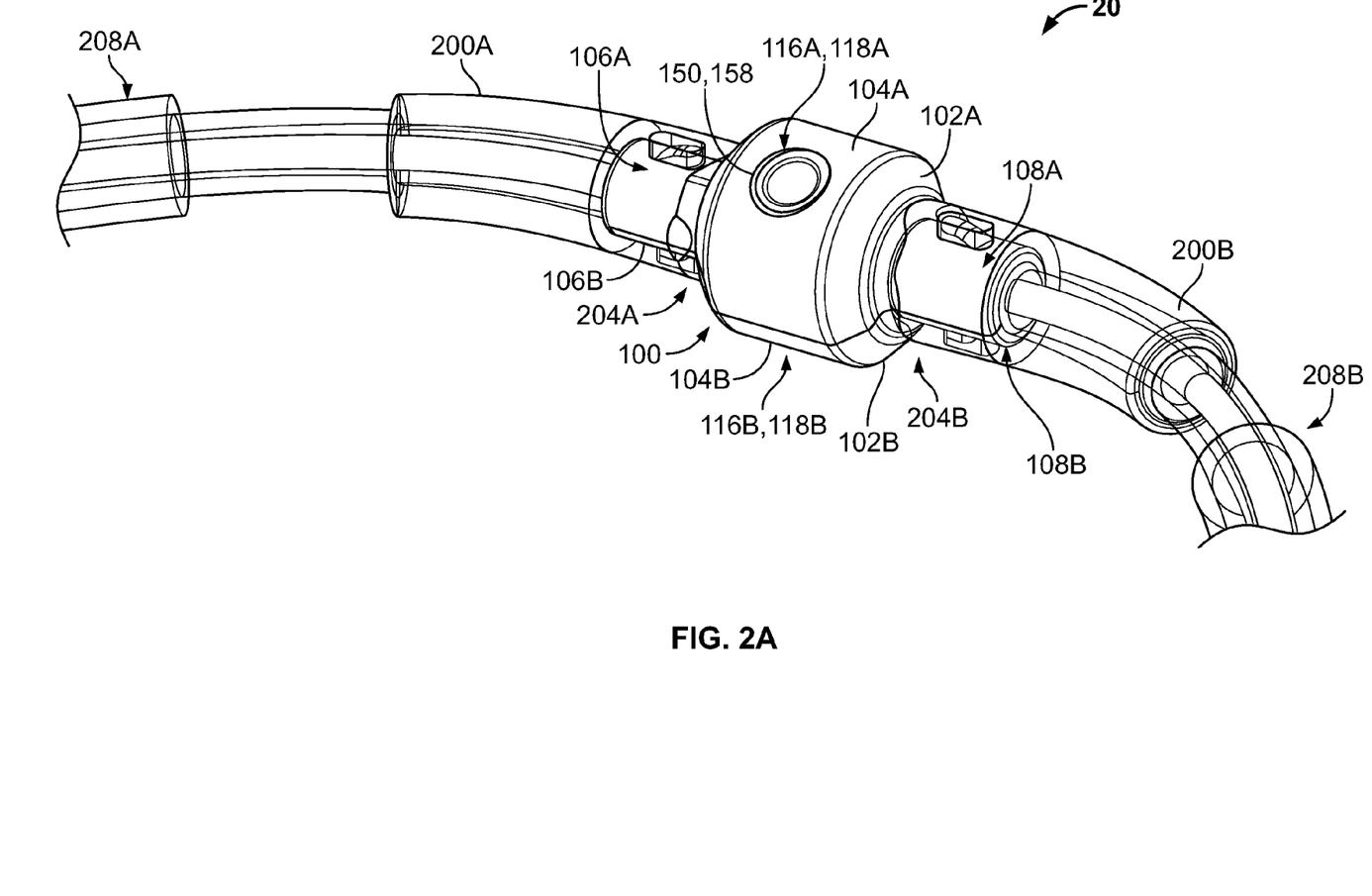
FIG. 2A is a close-up assembled view of an embodiment of the present adjustment assembly.

In FIG. 2A, a close-up view of adjustment assembly 20 according to one embodiment is shown, including a gearbox housing 100 comprised of a first gearbox shell 102A and a second gearbox shell 102B. As discussed in further detail below, first gearbox shell 102A and second gearbox shell 102B are held together by a first gearbox sleeve 200A and a second gearbox sleeve 200B. First gearbox sleeve 200A includes a first end 204A and a second end 208A. Second gearbox sleeve 200B includes a first end 204B and a second end 208B. In this embodiment, first and second gearbox shells 102A, 102B are generally similar in construction to one another. Accordingly, like reference numerals, appended by 'A' or 'B,' are used herein to designate similar features of first and second gearbox shells 102A, 102B, respectively. For example, reference numeral 104A designates a center portion of first gearbox shell 102A, while reference numeral 104B designates a center portion of second gearbox shell 102B.

Figure 2B:
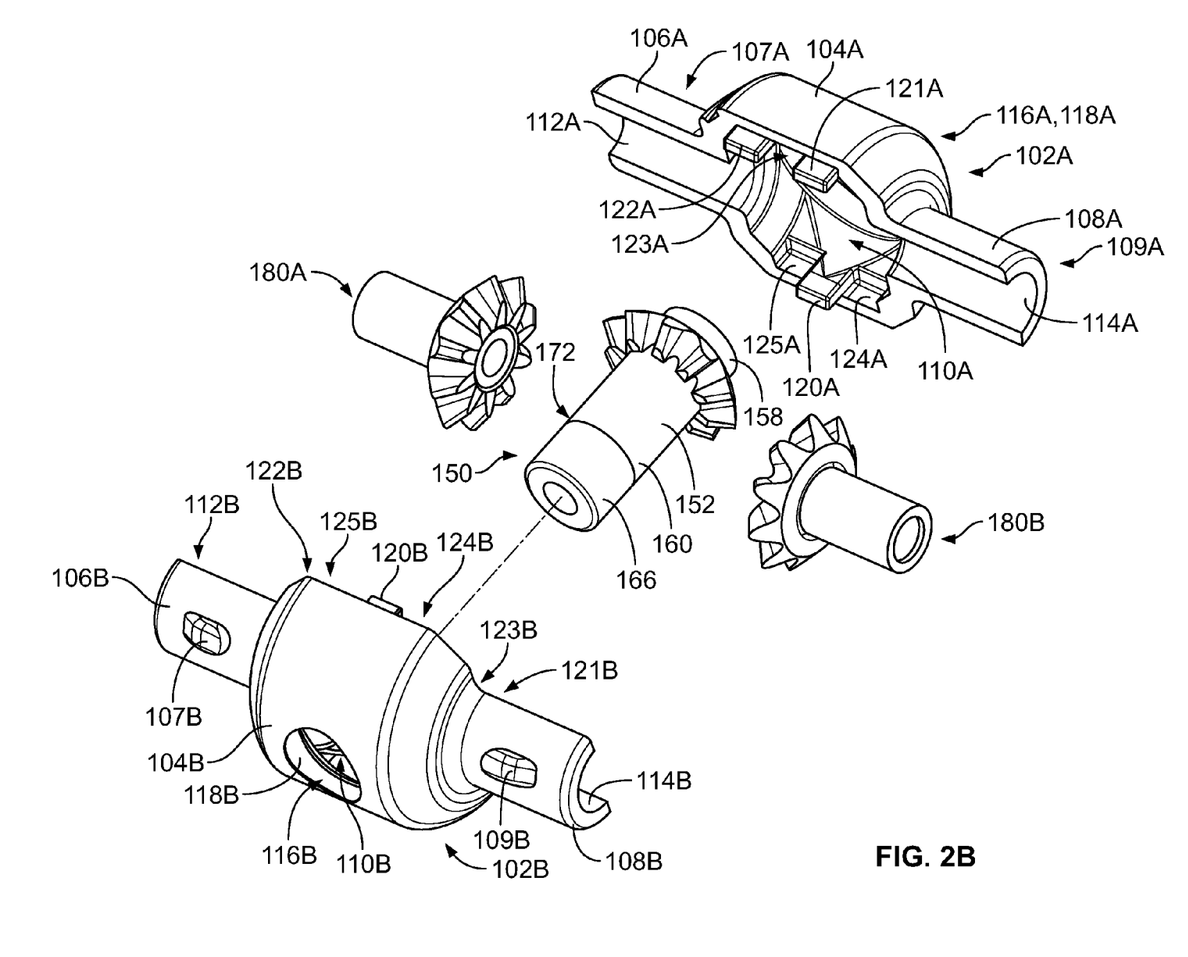
FIG. 2B is an exploded view of a gearbox of an embodiment of the present adjustment assembly.

Referring to FIG. 2B, an exploded view of gearbox housing 100 according to one illustrative embodiment of the present adjustment assembly is shown. First gearbox shell 102A includes a center portion 104A with a first lateral portion 106A and a second lateral portion 108A respectively extending from opposite sides thereof. A substantially hollow cavity 110A is formed within center portion 104A. Second gearbox shell 102B includes a center portion 104B with a first lateral portion 106B and a second lateral portion 108B respectively extending from opposite sides thereof. Center portion 104B includes an opening 116B having an inner surface 118B formed therein. A first projection 107B is included on an exterior surface of first lateral portion 106B and a second projection 109B is included on an exterior surface of second lateral portion 108B.

In the embodiment shown, first gearbox shell 102A and second gearbox shell 102B are generally similar in construction to one another and are made from the same material. For example, first gearbox shell 102A also includes an opening 116A (see FIG. 5A) in center portion 104A that is generally similar to opening 116B in center portion 104B of second gearbox shell 102B. Opening 116A in center portion 104A includes an inner surface 118A similar to inner surface 118B of opening 116B. Similarly, first gearbox shell 102A includes first and second projections 107A, 109A on first and second lateral portions 106A, 108A, respectively, which projections 107A, 109A are generally similar to projections 107B, 109B, respectively. Center portion 104B of second gearbox shell 102B also forms a substantially hollow cavity 110B therein, which cavity 110B is generally similar to cavity 110A formed by center portion 104A of first gearbox shell 102A.

Still with reference to FIG. 2B, first gearbox shell 102A includes a set of tabs 120A, 121A, 122A and a set of recesses 123A, 124A, 125A. In this embodiment, second gearbox shell 102B includes a corresponding set of tabs 120B, 121B, 122B, which is generally similar to the set of tabs 120A, 121A, 122A of first gearbox shell 102A, and a set of recesses 123B, 124B, 125B, which is generally similar to the set of recesses 123A, 124A, 125A of first gearbox shell 102A. Tabs 120B, 121B, and 122B are adapted to respectively interlock with recesses 123A, 124A, and 125A, and tabs 120A, 121A, 122A are adapted to respectively interlock with recesses 123B, 124B, and 125B to couple first gearbox shell 102A to second gearbox shell 102B, forming gearbox housing 100. In this embodiment, tab 120A is adapted to interlock with recess 123B, tab 121A is adapted to interlock with recess 124B, and tab 122A is adapted to interlock with recess 125B. Likewise, tab 120B is adapted to interlock with recess 123A, tab 121B is adapted to interlock with recess 124A, and tab 122B is adapted to interlock with recess 125A. This interlocking of tabs 120A-122A with recesses 123B-125B and tabs 120B-122B with recesses 123A-125A can enhance the reliability of the engagement between first and second gearbox shells 102A, 102B when first and second gearbox shells 102A, 102B are coupled to one another to form gearbox housing 100. As discussed in further detail below, a set of gears, or gear assembly, is provided within gearbox housing 100, including a center gear 150, a first driven gear 180A, and a second driven gear 180B. By making the gearbox shells 102A, 102B generally similar to one another in construction, increased efficiency in manufacturing gearbox shells 102A, 102B can be achieved, for example, with regard to the time and/or cost required to manufacture or mass-produce the gearbox shells. This construction can also facilitate a more reliable engagement between the gearbox shells 102A, 102B when coupled to one another to form gearbox housing 100. However, the gearbox shells 102A, 102B may be of different constructions and/or made of different materials from one another as desired.

Figure 2C:
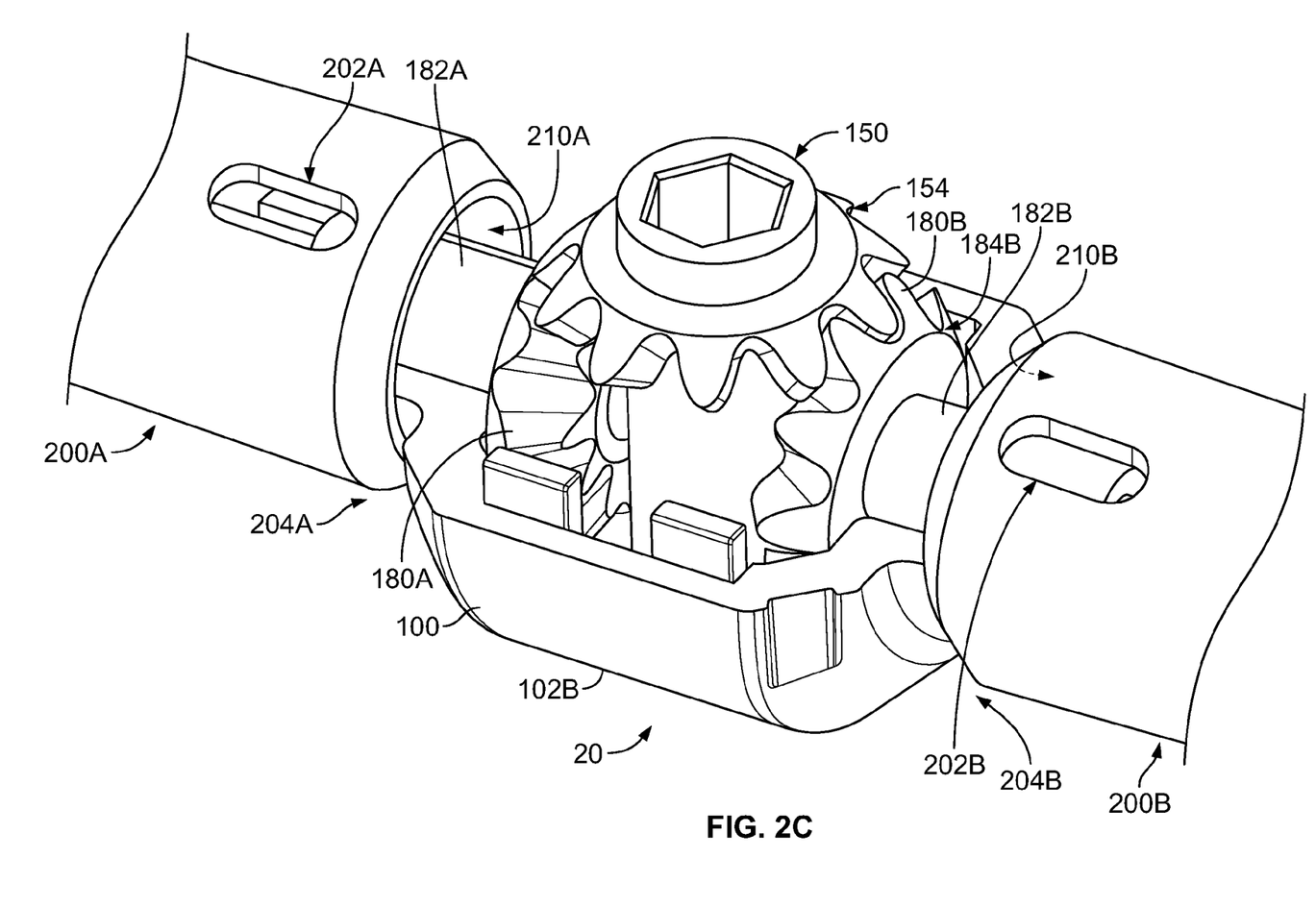
FIG. 2C is a close-up, assembled view of an embodiment of the present adjustment assembly with one gearbox shell removed.

FIG. 2C provides a close-up view of an exemplary embodiment of adjustment assembly 20 with one gearbox shell removed for clarity of illustration. In this embodiment, the gear assembly includes center gear 150, first driven gear 180A, and second driven gear 180B, each disposed at least partially within gearbox housing 100. As discussed in further detail below, center gear 150 engages each of first driven gear 180A and second driven gear 180B, such that when center gear 150 is rotated, for example by an external adjustment tool 300 (see FIG. 3E), first and second driven gears 180A, 180B are rotated by center gear 150.

Referring to FIGS. 3A-3E, center gear 150 includes a shaft portion 152 and a gear portion 154. Gear portion 154 includes gear teeth 156 surrounding the shaft portion 152. Shaft portion 152 includes a top portion 158 and a bottom portion 160. A shaped hole 165 is formed in top portion 158. As discussed in further detail below, the hole 165 may include a hexagonal shape as shown, or any other shape suitable for engaging an adjustment mechanism 302 having a corresponding shape, such that the adjustment mechanism 302 is substantially incapable of rotating with respect to center gear 150 while engaging hole 165. In one embodiment, a hollow internal cavity 162 is formed within center gear 150 in communication with hole 165.

Figure 3A:
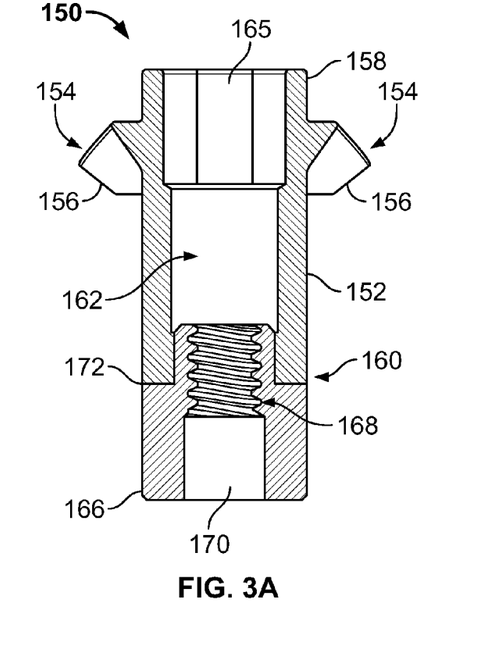
FIG. 3A is a cross-sectional view of a center gear of an embodiment of the present adjustment assembly.

Center gear 150 also includes a threaded insert 166 including a threaded bore 170 formed therein. A set of internal threads 168 is formed along at least a portion of the length of threaded bore 170. In the embodiment shown, threaded insert 166 and bottom portion 160 are welded to one another by one or more weld joints 172 therebetween. In some embodiments, one or more weld joints 172 may be provided, and/or may extend along all or a part of the area of engagement between bottom portion 160 and threaded insert 166.

Threads 168 of insert 166 are adapted to engage an engagement element 304 of adjustment tool 300 (see FIG. 3E) used to rotate center gear 150 to adjust the size and/or shape of adjustable prosthetic anatomical device 10. By engaging the engagement element 304 of the adjustment tool 300, threads 168 of threaded insert 166 can provide a more reliable engagement between the adjustment tool 300 and the adjustable device 10 during a surgical procedure in which the size and/or shape of an anatomic orifice or lumen is changed using the adjustment tool 300. Examples of suitable adjustment tools and engagement elements are provided in U.S. Provisional Patent Application Ser. Nos. 60/878,068 and 61/527, 801 and in United States Patent Application Publication No. 2011/0066231, the entire disclosures of which are each incorporated herein by reference.

In the illustrative embodiment shown, threads 168 are provided in insert 166, which is a separate piece welded to shaft portion 152 at one or more weld joints 172. However, in other embodiments, threads 168 may be incorporated directly into center gear 150 as an integral one-piece construction, such that there is no need for a separate piece and, therefore, no need for a weld joint. Such an integral one-piece construction can advantageously reduce the time and/or cost of manufacturing or mass-producing center gear 150, as well as facilitate a more reliable engagement with the adjustment tool 300.

In a preferred embodiment, shaft portion 152 and gear portion 154 of center gear 150 are integrally molded with one another as a single part, such that it is not necessary to include a connection (such as a weld joint) connecting gear portion 154 to shaft portion 152.

As discussed in further detail below, gear teeth 156 are adapted to engage gear teeth of driven gears 180A, 180B such that the rotation of center gear 150 is transmitted via driven gears 180A, 180B to another part of adjustable prosthetic anatomical device 10 to adjust the size and/or shape of the device. Accordingly, center gear 150 is rotated by a user applying a rotational force to the adjustment tool 300 while an adjustment mechanism 302 of the adjustment tool 300 is in engagement with hole 165 of center gear 150. In this regard, hole 165 of center gear 150 is shaped to engage adjustment mechanism 302 such that adjustment mechanism 302 is substantially incapable of rotating with respect to center gear 150 when the adjustment mechanism 302 is in engagement with hole 165. (See FIG. 3E.) For example, in the embodiment shown, hole 165 includes a hexagonal shape, which is adapted to engage a similarly hexagonally shaped adjustment mechanism. However, hole 165 may include another shape, such as a square, rectangle, hexagon, pentagon, other quadrilateral, polygonal, or multilateral shape, one or a plurality of teeth, ridges, or engagement protrusions and/or recesses extending radially outward or inward, common or custom-made screwdriver head shapes, other similar and appropriate shapes, or any combination thereof. Alternatively, hole 165 may include a different shape adapted to engage one or more different types of adjustment mechanisms.

The rotational force applied to the adjustment tool 300 while the adjustment tool 300 is in engagement with center gear 150 via hole 165 (see FIG. 3E) is in turn transmitted from shaft portion 152 to gear portion 154 for transmission to driven gears 180A, 180B by virtue of the engagement between gear portion 154 and the gear portions of driven gears 180A, 180B. Therefore, a weld joint between shaft portion 152 and gear portion 154 would be directly in the load path of the above-described force transmission, requiring the adjusting force to be applied to the weld joint and making that weld joint vulnerable to breaking during the adjustment procedure. Such vulnerability would create a point of potential failure in adjustment assembly 20.

Advantageously, in this embodiment of the present adjustment assembly, shaft portion 152 and gear portion 154 of center gear 150 are integrally molded with one another as a single part, such that it is not necessary to include a weld joint therebetween. This construction can lead to increased efficiency in the production of center gear 150. As discussed in further detail below, the same is true of driven gears 180A, 180B according to an embodiment of the present adjustment assembly. Eliminating the weld joints between the gear portions and the shaft portions of the respective gears also advantageously removes points of potential failure from the adjustment assembly, thus reducing the likelihood of a failure or breakage in the adjustment assembly.

Figure 3B:
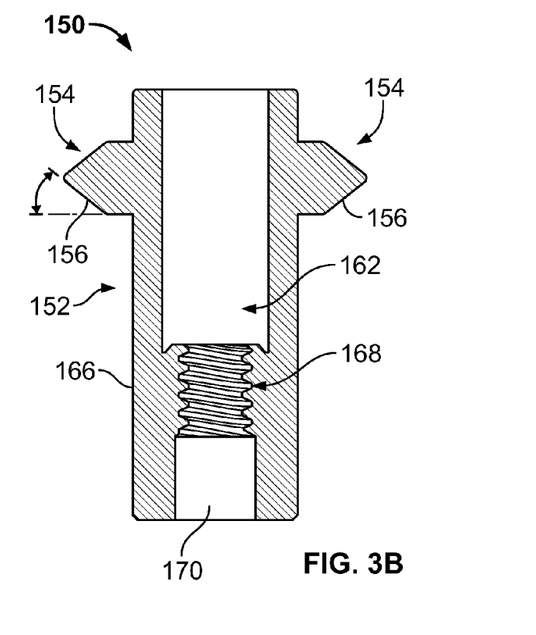
FIG. 3B is a cross-sectional view of a center gear of another embodiment of the present adjustment assembly.

FIG. 3B shows a cross-sectional view of center gear 150 according to another embodiment, in which shaft portion 152 and gear portion 154 are formed together as a single, integrally molded part with one another. Internal cavity 162 extends within center gear 150 over the length of shaft portion 152, and is in communication with threaded bore 170 of insert 166. Accordingly, as shown in FIG. 3E, when adjustment mechanism 302 of adjustment tool 300 is inserted into cavity 162 through hole 165, engagement element 304 of the adjustment mechanism 302 can readily engage threads 168 of threaded insert 166 to couple adjustment tool 300 to adjustment assembly 20. In the embodiment shown, engagement element 304 includes a set of threads 306 adapted to engage threads of threaded insert 166. In other embodiments, another suitable and appropriate engagement element could be used.

Figure 3C:
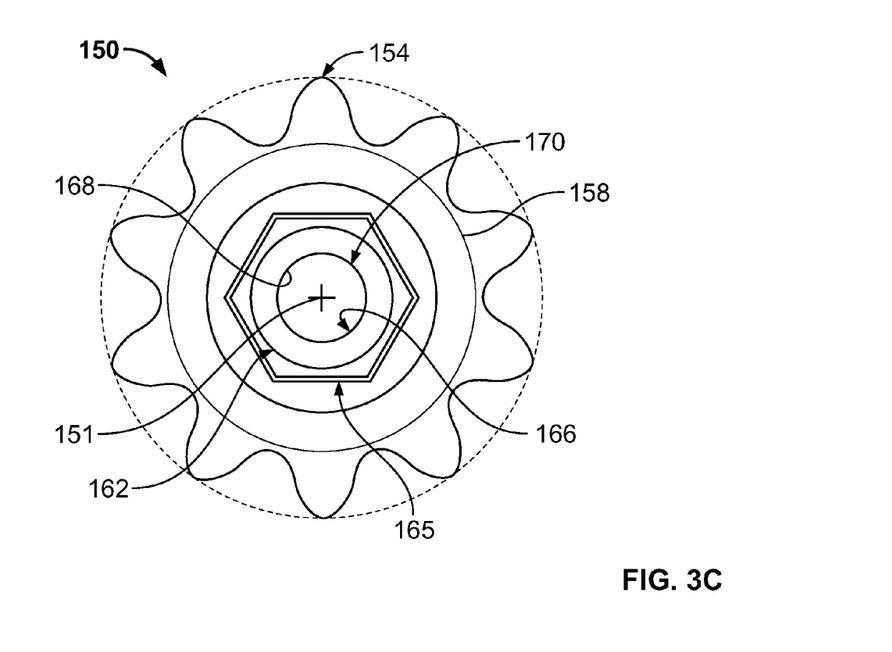
FIG. 3C is a top plan view of a center gear of an embodiment of the present adjustment assembly.

In FIG. 3C, a top view of center gear 150 is shown, with hole 165 formed in top portion 158 of shaft portion 152. Hole 165 is in communication with a top end of cavity 162, while a bottom end of cavity 162 communicates with bore 170 of insert 166. Hole 165 may include any shape that is adapted to engage an adjustment mechanism having a corresponding shape, such as adjustment mechanism 302 of adjustment tool 300. For example, hole 165 may include any such shape, such as a square, rectangle, other quadrilateral, polygon, pentagon, hexagon, or multilateral shape, one or a plurality of teeth, ridges, or engagement protrusions and/or recesses extending radially outward or inward, common or custom-made screwdriver head shapes, other similar and appropriate shapes, or any combination thereof. In the embodiment shown, hole 165 is shaped as a hexagon, such that hole 165 can be engaged by a correspondingly hexagonally shaped adjustment mechanism of an adjustment tool. (See also, FIGS. 2C, 3E.) Alternatively, hole 165 may include a different shape adapted to engage one or more different types of adjustment mechanisms.

In the illustrative embodiment shown in FIGS. 3A-3E, by virtue of the hexagonal shape of hole 165, adjustment mechanism 302 of adjustment tool 300 is adapted to engage hole 165 such that adjustment mechanism 302 is substantially incapable of rotating relative to center gear 150 while the adjustment mechanism 302 is inserted within the hexagonal hole 165. Therefore, with reference to FIG. 3E, to rotate center gear 150, a user can insert adjustment mechanism 302 having a shape corresponding to the shape of hole 165 into hole 165 and subsequently manipulate the adjustment tool 300 to rotate the adjustment mechanism 302 relative to an axis 151 of center gear 150. This rotation of the adjustment mechanism 302 while in engagement with hole 165 rotates center gear 150 relative to axis 151, which rotation is in turn transmitted to driven gears 180A, 180B by virtue of the engagement between gear teeth 156 of gear portion 154 and gear teeth 186A, 186B of the gear portions 184A, 184B of driven gears 180A, 180B. The arrangement of center gear 150 and driven gears 180A, 180B in gearbox housing 100, as well as the engagement of center gear 150 with each of driven gears 180A, 180B, during this process is also depicted, for example, in FIG. 2C.

Figure 3D:
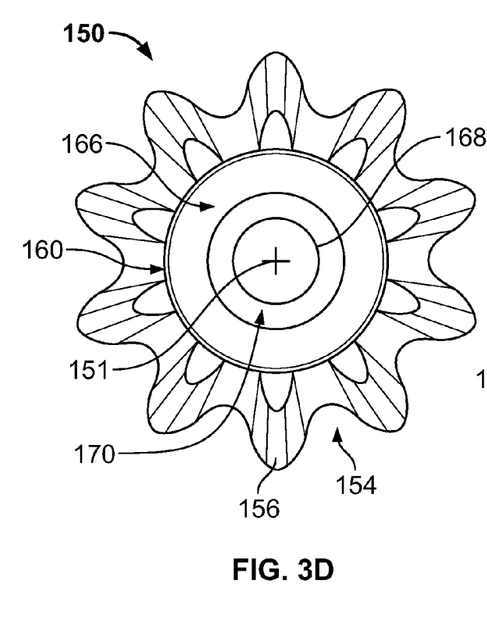
FIG. 3D is a bottom plan view of a center gear of an embodiment of the present adjustment assembly.
Figure 3E:
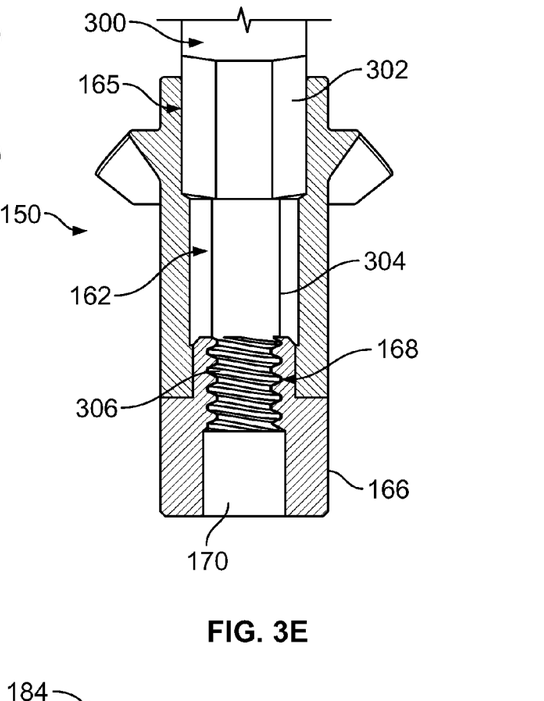
FIG. 3E is a cross-sectional view of a center gear of an embodiment of the present adjustment assembly in engagement with an adjustment tool.

FIG. 3D provides a bottom plan view of center gear 150, including insert 166 joined to shaft portion 152. Bore 170 of insert 166, including threads 168 formed therein, is also shown. In the embodiment shown, gear portion 154 is formed as a bevel gear, with gear teeth 156 thereof arranged at an angle with respect to axis 151 and adapted to engage gear teeth arranged at an angle to their own longitudinal axis. However, other embodiments may include other types of gears or gear teeth arrangements, such as a worm and worm gear arrangement and/or one or more spur gears.

In this embodiment, gear portion 154 is located adjacent top portion 158 of shaft portion 152, such that space is provided below gear portion 154 for the gear portions of driven gears 180A, 180B to be arranged. Accordingly, this embodiment includes gear teeth 156 of gear portion 154 angled downward, i.e., toward bottom portion 160 of shaft portion 152. However, in other embodiments, gear portion 154 may be arranged differently. For example, gear portion 154 could be arranged at or adjacent to lower portion 160 of shaft 152, such that space for the gear portions of driven gears 180A, 180B to be arranged is provided above gear portion 154. In such an embodiment, gear teeth 156 of gear portion 154 would angle upward, i.e., toward top portion 158 of shaft portion 152, to engage the gear teeth 186A, 186B of the gear portions 184A, 184B of driven gears 180A, 180B.

In FIGS. 4A-4D, a representative driven gear 180 is shown, which represents the features of driven gears 180A, 180B according to one exemplary embodiment in which driven gears 180A, 180B are generally similar in construction to one another. Accordingly, common reference numerals are used herein to designate the features of first driven gear 180A and second driven gear 180B, appended by characters 'A' and 'B', respectively. For example, reference numeral 182 designates a shaft portion of representative driven gear 180, with reference numeral 182A designating a shaft portion of first driven gear 180A and reference numeral 182B designating a shaft portion of second driven gear 180B. The present description of representative driven gear 180 is equally applicable to each of first and second driven gears 180A, 180B.

Representative driven gear 180 includes shaft portion 182 and a gear portion 184. Gear portion 184 includes gear teeth 186, which are adapted to engage gear teeth 156 of center gear 150. As best shown in the cross-sectional view of driven gear 180 depicted in FIG. 4B, driven gear 180 is preferably, though not necessarily, formed as an integrally molded part, such that shaft portion 182 and gear portion 184 are formed from a single, contiguous piece of material with one another. Preferably, center gear 150 and driven gears 180A, 180B are each manufactured by a metal injection molding (MIM) process, which can advantageously reduce the time and cost associated with the manufacturing thereof. However, center gear 150 and/or one or both of driven gears 180A, 180B may alternatively be made from a different manufacturing process, such as milling, casting, or other suitable manufacturing processes, or a combination thereof. Gear portion 184 is preferably, but not necessarily, arranged to substantially align with a first end 181 of shaft portion 182, such that a first end 185 of gear portion 184 substantially coincides with first end 181 of shaft portion 182. As discussed in detail above with respect to center gear 150, forming driven gear 180 as an integrally molded part removes the need for a weld joint or other type of joint connecting gear portion 184 to shaft portion 182, which joint would otherwise be directly in the load path of the force transmission from center gear 150 to driven gears 180A, 180B. Advantageously, removing the need for such a joint removes a point of potential failure in adjustment assembly 20, which reduces the likelihood of failure or breakage in adjustment assembly 20. This embodiment also includes a substantially hollow cavity 188 formed within driven gear 180.

Figure 4A:
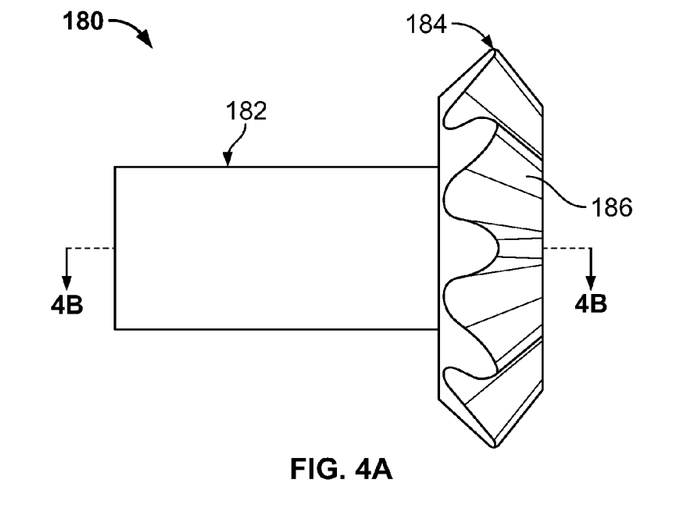
FIG. 4A is a side elevation view of a driven gear of an embodiment of the present adjustment assembly.
Figure 4B:
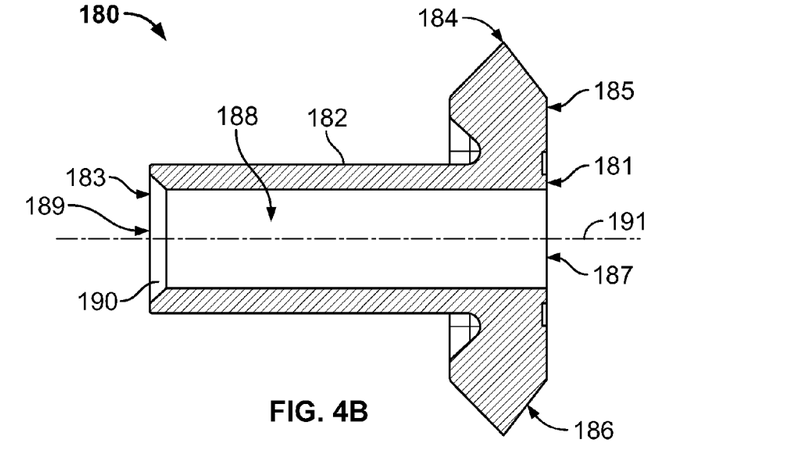
FIG. 4B is a cross-sectional view of the driven gear shown in FIG. 4A taken along section 4B-4B thereof.

A gradual transition 190 is included around a periphery of second end 183 of driven gear 180. For example, gradual transition 190 is shown as a chamfer cut. However, in other embodiments, gradual transition 190 may include one or more miter cuts, beveled surfaces, rounded edges, other appropriate transitions, or a combination thereof. In still further embodiments, gradual transition 190 may be omitted, such that a corner or other substantially abrupt transition (not shown) is formed at second end 183. Gradual transition 190 can provide various advantages, such as avoiding stress concentrations in driven gear 180 and/or the transmission mechanism. Including gradual transition 190 can also lead to reductions in the time and/or cost of manufacturing and/or mass-producing driven gear 180. Additionally, gradual transition 190 can facilitate a more reliable engagement between driven gears 180A, 180B and a transmission mechanism (not shown). For example, gradual transition 190 can facilitate and enhance the speed and simplicity of an assembly process in which the transmission mechanism is accommodated within the inner diameter of cavity 188. In one embodiment, the transmission mechanism can comprise a drive cable. As discussed in further detail below, the transmission mechanism can be provided to transmit the rotation of driven gears 180A, 180B to another part of adjustable prosthetic anatomical device 10.

In the illustrative embodiment shown, cavity 188 is substantially cylindrical and extends along the entire length of shaft portion 182 to form a first opening 187 at first end 181 and a second opening 189 at second end 183 of driven gear 180. Cavity 188 can be designed to interact with a transmission mechanism (not shown), such as a cable, rod, wire, or other similar and appropriate transmission mechanism, such that the transmission mechanism transmits the rotation of driven gear 180 to another part, device, assembly, or mechanism of adjustable prosthetic anatomical device 10 to accomplish the adjustment to the size and/or shape of the device. U.S. Provisional Patent Application Ser. No. 60/878,068 and United States Patent Application Publication No. 2011/0066231 each provide illustrative examples of suitable transmission mechanisms.

In other embodiments, one or both of first and second ends 181, 183 may be entirely or partially closed, such as by one or more sheets, plates, or surfaces (not shown) extending over first end 181 and/or second end 183. In addition, cavity 188 may extend over only one or more portions of the length of shaft portion 182, rather than the entire length thereof. In still further embodiments, shaft portion 182 may be formed as a substantially solid part, such that all or part of cavity 188 is not formed therein.

Figure 4C:
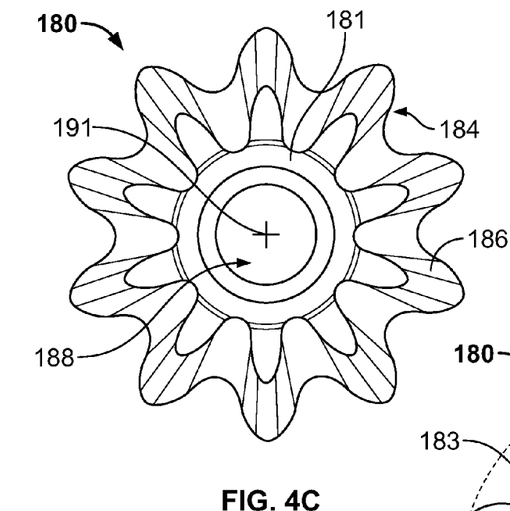
FIG. 4C is a top plan view of a driven gear of an embodiment of the present adjustment assembly.

FIG. 4C shows driven gear 180 as viewed along a longitudinal axis 191 thereof from first end 181, such that gear teeth 186 of gear portion 184 are shown. As discussed previously, gear teeth 186 are adapted to engage gear teeth 156 of center gear 150 such that rotation of center gear 150 causes driven gear 180 to rotate therewith. In turn, the rotation of driven gear 180 is transmitted by the transmission mechanism to another part of adjustable prosthetic anatomical device 10 to adjust the size and/or shape of the adjustable prosthetic anatomical device. Preferably, gear portion 184 is formed as a bevel gear, such that gear teeth 186 are formed at an angle with respect to longitudinal axis 191 and adapted to engage gear teeth formed at an angle to their own longitudinal axis. However, in other embodiments, gear portion 184 may be formed differently, such as including a worm or worm gear arrangement, spur gear, or other appropriate force transmission arrangement.

Figure 4D:
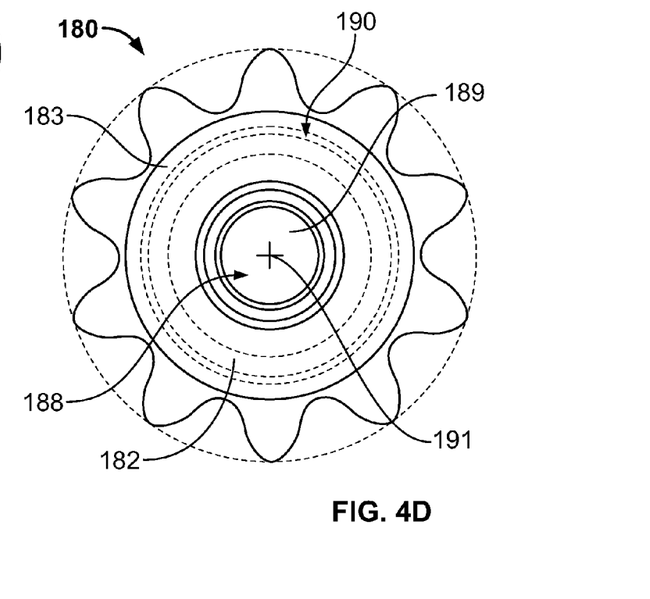
FIG. 4D is a bottom plan view of a driven gear of an embodiment of the present adjustment assembly.

Referring to FIG. 4D, driven gear 180 is shown according to a view along longitudinal axis 191 thereof from second end 183. Gradual transition 190 is formed at second end 183. Second opening 189 is formed at second end 183, with cavity 188 extending along the entire length of driven gear 180.

Figure 5A:
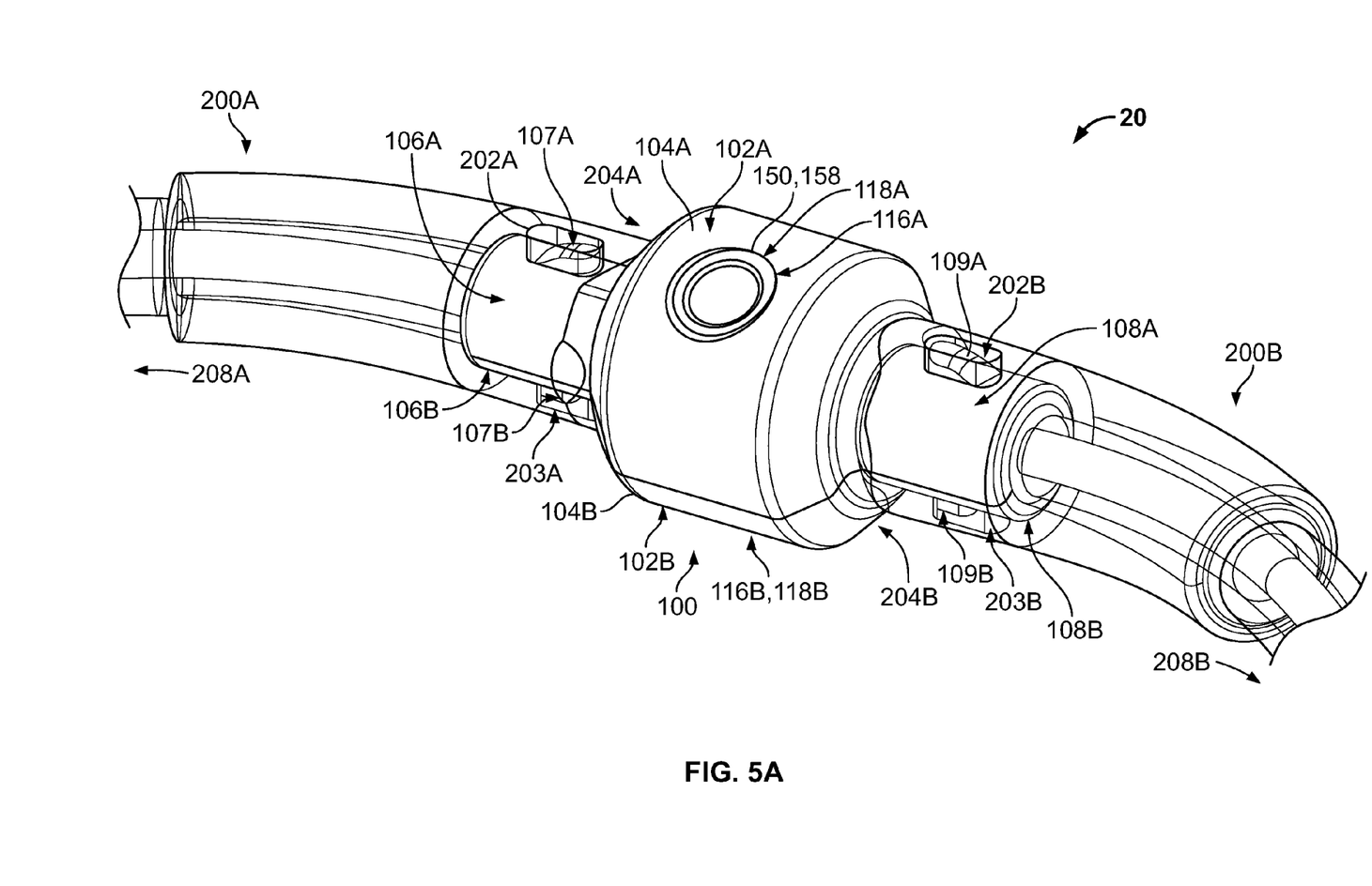
FIG. 5A is a perspective view of a gearbox housing and two gearbox sleeves of an embodiment of the present adjustment assembly.
Figure 5B:
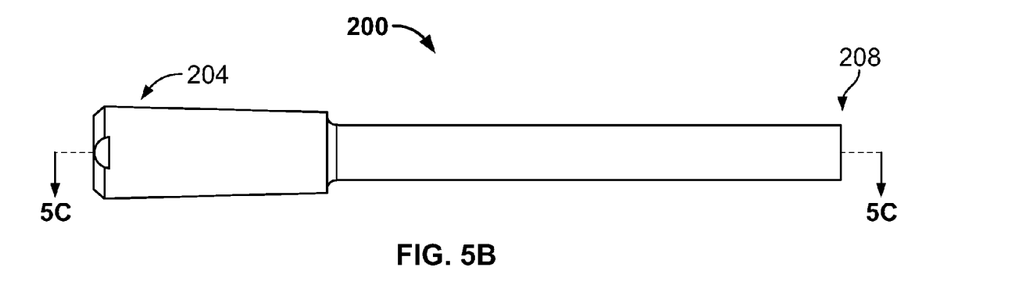
FIG. 5B is a side elevational view of a gearbox sleeve of an embodiment of the present adjustment assembly.
Figure 5C:
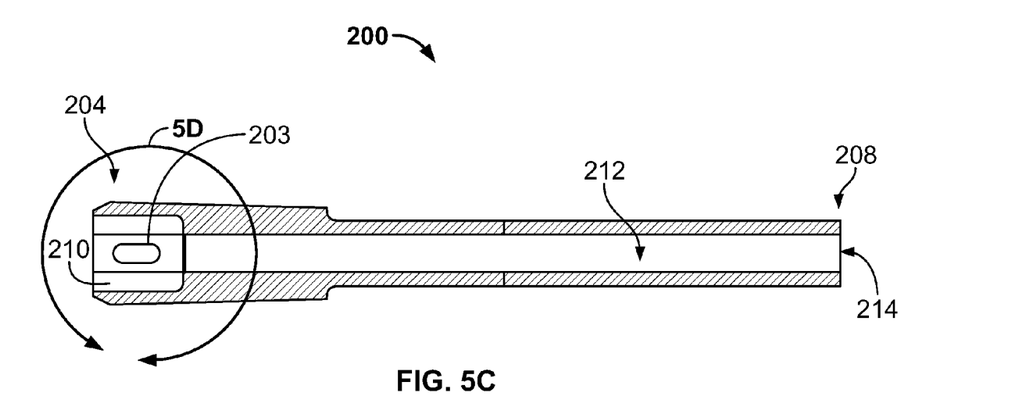
FIG. 5C is a cross-sectional view of the gearbox sleeve shown in FIG. 5B taken along section 5C-5C thereof.
Figure 5D:
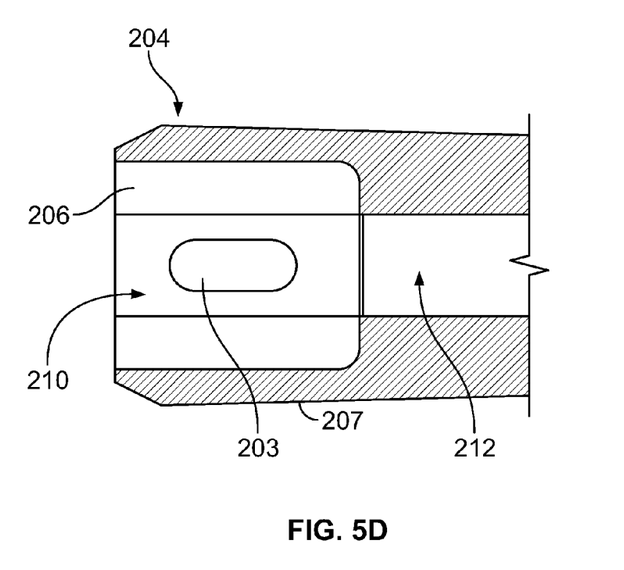
FIG. 5D is a close-up, top cross-sectional view of an end of a gearbox sleeve according to an embodiment of the present adjustment assembly.

In FIG. 5A, gearbox housing 100 is shown, formed by first and second gearbox shells 102A, 102B coupled to one another and held together by first gearbox sleeve 200A and second gearbox sleeve 200B. In this illustrative embodiment, first and second gearbox sleeves 200A, 200B are generally similar in construction to one another. Accordingly, common reference numerals are used herein to designate the features of first gearbox sleeve 200A and second gearbox sleeve 200B, appended by characters 'A' and 'B', respectively. For example, reference numeral 204A designates a first end of first gearbox sleeve 200A, while reference numeral 204B designates a first end of second gearbox sleeve 200B. Additionally, FIGS. 5B-5D depict various views of a representative gearbox sleeve 200, the present description of which is equally applicable to each of first and second gearbox sleeves 200A, 200B. In such figures, like reference numerals are used to designate the features of the representative gearbox sleeve 200 corresponding to the features of first and second gearbox sleeves 200A, 200B. For example, in FIGS. 5B-5D, reference numeral 204 designates a first end of representative gearbox sleeve 200, the description of which is equally applicable to first ends 204A, 204B of first and second gearbox sleeves 200A, 200B, respectively.

First gearbox sleeve 200A includes first end 204A and a second end 208A. Second gearbox sleeve 200B includes a first end 204B and a second end 208B. Second ends 208A, 208B are each adapted to act as a rail to accommodate another portion of adjustable prosthetic anatomical device 10 adapted to slide along second ends 208A, 208B. For example, in one embodiment, second ends 208A, 208B are adapted to accommodate a spar of an adjustable prosthetic anatomical device, such as an adjustable annuloplasty ring or other adjustable prosthetic anatomic valve device, such that first and second gearbox sleeves 200A, 200B join gearbox housing 100 to the spar of the adjustable prosthetic anatomical device.

FIG. 5B shows a side elevational view of representative gearbox sleeve 200, including a first end 204 and a second end 208. In this view, gearbox sleeve 200 is shown as being substantially straight. However, when used to assemble adjustable prosthetic device 10, gearbox sleeve 200 may include one or more bends, curves, joints, elbows, vertices, undulations, or other similar arrangements provided along the length thereof as desired. (See, e.g., FIG. 2A).

In FIG. 5C, a cross-sectional view of gearbox sleeve 200 is shown, taken along section 5C-5C of FIG. 5B. In the embodiment shown, gearbox sleeve 200 is an integrally molded part formed by injection molding into a single piece of material. In this regard, gearbox sleeve 200 may be made from any suitable polymer, plastic, metal, or other similar and appropriate material, or a combination thereof. In other embodiments, gearbox sleeve 200 may be made from multiple subparts combined to one another, some or all of which may be made by other machining or manufacturing processes, such as casting, milling, drilling, lathing, sanding, any other suitable machining or manufacturing process, or a combination thereof.

Still with reference to FIG. 5C, at first end 204, a substantially hollow internal cavity 210 is formed within first end 204 of gearbox sleeve 200. FIG. 5D shows an enlarged view of first end 204 of gearbox sleeve 200, including cavity 210 formed therein and having an inner surface 206. First end 204 also includes an outer surface 207. Cavity 210 is designed to accommodate corresponding lateral portions of first and second gearbox shells 102A, 102B therein when first and second gearbox shells 102A, 102B are coupled to one another. For example, and as best shown in FIG. 2A, when first and second gearbox shells 102A, 102B are coupled together to form gearbox housing 100, first lateral portions 106A, 106B of first and second gearbox shells 102A, 102B, respectively, are coupled to one another, and can be accommodated together within a cavity 210A formed in first end 204A of first gearbox sleeve 200A to hold gearbox shells 102A, 102B together. Similarly, second lateral portions 108A, 108B of first and second gearbox shells 102A, 102B, respectively, are coupled to one another, and can be accommodated together within a cavity 210B formed in first end 204B of second gearbox sleeve 200B.

Referring again to FIG. 5C, a substantially hollow channel 212 is included within gearbox sleeve 200. In the exemplary embodiment shown, channel 212 is in communication with cavity 210 and extends along the entire length of gearbox sleeve 200 to second end 208, such that an opening 214 is formed at second end 208. Channel 212 is designed to accommodate a transmission mechanism (not shown) that interacts with at least one of driven gears 180A, 180B to transmit the rotation thereof to another part of adjustable prosthetic anatomical device 10 to actuate that other part to accomplish the adjustment to the size and/or shape of the adjustable prosthetic anatomical device 10.

With reference again to FIG. 5A, first gearbox sleeve 200A includes an opening 202A adjacent first end 204A thereof and second gearbox sleeve 200B includes an opening 202B adjacent first end 204B thereof. As shown in FIGS. 5C-5D, representative gearbox sleeve 200 also includes a second opening 203 adjacent first end 204 thereof, which represents second openings 203A, 203B formed adjacent first ends 204A, 204B and opposite first slots 202A, 202B, respectively. Although openings 202A, 202B, 203A, 203B are depicted as slots in the embodiment shown, one or more of such openings may, in other embodiments, include another type of opening, for example, a bore, an orifice, an aperture, a hole, or any other suitable and appropriate type of opening adapted to engage a respective projection of a gearbox shell.

In the embodiment shown, openings 202 and 203 are each arranged and designed to accommodate a respective one of the projections of first or second gearbox shells 102A, 102B (see FIG. 2A), which can provide increased reliability and security in the engagement between gearbox housing 100 and first and second gearbox sleeves 200A, 200B. For example, as best shown in FIG. 5A, first and second projections 107A, 109A of first gearbox shell 102A respectively engage first opening 202A of first gearbox sleeve 200A and first opening 202B of second gearbox sleeve 200B. Likewise, although not shown in detail, first and second projections 107B, 109B of second gearbox shell 102B respectively engage second opening 203A of first gearbox sleeve 200A and second opening 203B of second gearbox sleeve 200B.

In the embodiment shown, openings 202 and 203 each extend through the entire thickness of first end 204, from inner surface 206 of cavity 210 to outer surface 207. However, in other embodiments, one or more of openings 202 and/or 203 may only extend from inner surface 206 partially through the thickness of first end 204, to instead form a recess, dimple, depression, impression, indentation, or other similar void adapted to accommodate a corresponding one of projections 107A, 107B, 109A, 109B.

In a preferred embodiment, the engagements between gearbox housing 100 and first and second gearbox sleeves 200A, 200B are provided by virtue of an interference fit between the respective lateral portions of gearbox housing 100 and cavities 210A, 210B of first and second gearbox sleeves 200A, 200B. Thus, when first lateral portions 106A, 106B are coupled to one another and inserted into cavity 210A, first end 204A of first gearbox sleeve 200A temporarily stretches to allow first lateral portions 106A, 106B to be inserted far enough to position and align projections 107A, 107B to engage openings 202A, 203A, respectively. When projections 107A, 107B are positioned and aligned to respectively engage openings 202A, 203A, first end 204A is restored to its undeformed size and shape. In this illustrative embodiment, lateral portions 108A, 108B are similarly accommodated within cavity 210B of second gearbox sleeve 200B, such that projections 109A, 109B respectively engage openings 202B, 203B of second gearbox sleeve 200B.

Gearbox sleeves 200A, 200B are made of a material having sufficient resilience to allow their first ends 204A, 204B to deform and restore to their natural shape to accommodate first lateral portions 106A, 106B in first end 204A and to accommodate second lateral portions 108A, 108B in first end 204B. For example, as discussed above, gearbox sleeves 200A, 200B may be made from any suitable polymer, plastic, metal, or other similar and appropriate material, or a combination thereof. Preferably, gearbox sleeves 200A, 200B are each made from the same material. Other embodiments may include gearbox sleeves 200A, 200B being made from different materials. While gearbox sleeves 200A, 200B are each preferably integrally formed from a single, contiguous piece of material, other embodiments may include either or both of gearbox sleeves 200A, 200B being made of multiple parts joined to one another, which parts may be made of the same or different materials as one another. Further embodiments may only include first ends 204A, 204B having sufficient resilience to stretch and restore to their undeformed size and shape.

When the lateral portions of gearbox shells 102A, 102B of gearbox housing 100 are accommodated within cavities 210A, 210B of first and second gearbox sleeves 200A, 200B, respectively, center gear 150 and first and second driven gears 180A, 180B are rotatably supported within gearbox housing 100. As best shown in FIG. 2C, center gear 150 and first and second driven gears 180A, 180B are each rotatably supported within gearbox housing 100 and are arranged such that gear portions 184A, 184B of first and second driven gears 180A, 180B, respectively, each engage gear portion 154 of center gear 150. For clarity of illustration, one gearbox shell 102A is not shown in FIG. 2C. In this embodiment, shaft portion 182A of first driven gear 180A is rotatably accommodated within first lateral portions 106A, 106B of first and second gearbox shells 102A, 102B, respectively. Shaft portion 182B of second driven gear 180B is similarly rotatably accommodated within second lateral portions 108A, 108B of first and second gearbox shells 102A, 102B, respectively. Accordingly, shaft portions 182A, 182B extend at least partially into cavities 210A, 210B, respectively. Although first and second driven gears 180A, 180B are shown in this embodiment as being arranged substantially coaxially with one another with their common longitudinal axis 191 substantially perpendicular to the rotational axis 151 of center gear 150, one or both of first and second driven gears 180A, 180B may, in other embodiments, be arranged differently in other embodiments, such as being arranged along different longitudinal axes, which axes may be parallel to one another, angled with respect to one another, intersecting, non-intersecting, and/or may be disposed in the same plane or in different planes.

Referring to FIG. 2B, a first surface 112A is formed on an inside surface of first lateral portion 106A of first gearbox shell 102A. An inside surface of second lateral portion 108A of first gearbox shell 102A includes a second surface 114A. Similarly, first lateral portion 106B and second lateral portion 108B of second gearbox shell 102B respectively include a first surface 112B and a second surface 114B formed on the insides thereof. During use of adjustment assembly 20, first surfaces 112A and 112B cooperate to provide a bearing surface for rotatably supporting driven gear 180A during rotation thereof. Likewise, second surfaces 114A and 114B cooperate to provide a bearing surface for rotatably supporting driven gear 180B during rotation thereof. Accordingly, driven gears 180A, 180B are each securely and reliably arranged and supported within gearbox housing 100 while being capable of rotation therein.

As best shown in FIGS. 2A, 2B, and 5A, according to one embodiment, opening 116A in first gearbox shell 102A includes inner surface 118A, while opening 116B in second gearbox shell 102B includes inner surface 118B. When center gear 150 is accommodated within gearbox housing 100, inner surfaces 118A and 118B provide bearing surfaces to rotatably support center gear 150. In the embodiment shown, top portion 158 of shaft portion 152 is rotatably accommodated by inner surface 118A of first gearbox shell 102A, while part or all of insert 166 of center gear 150 is accommodated by inner surface 118B of second gearbox shell 102B. In one embodiment, insert 166 is joined to shaft portion 152 by one or more weld joints 172 for rotation with shaft portion 152, such that rotatably accommodating insert 166 within opening 116B also rotatably supports center gear 150. In another embodiment in which the threaded portion of center gear 150 is formed as an integral part of shaft portion 152, lower portion 160 of shaft portion 152 is rotatably accommodated within opening 116B.

Referring to FIG. 3E, during operation of adjustment assembly 20 according to one embodiment, center gear 150 is engaged by adjustment tool 300 including engagement mechanism 304 adapted to engage threads 168 of threaded insert 166 and adjustment mechanism 302 adapted to engage hole 165 in top portion 158 of center gear 150. While engagement mechanism 304 engages threads 168 and adjustment mechanism 302 engages hole 165 of center gear 150, adjustment tool 300 is manipulated by a user (e.g., a surgeon) to rotate center gear 150 within gearbox housing 100. Gear teeth 156 of center gear 150 are in meshed engagement with gear teeth 186A of first driven gear 180A and with gear teeth 186B of second driven gear 180B. Therefore, when center gear 150 is rotated by the adjustment tool 300, first and second driven gears 180A, 180B are rotated by center gear 150. As discussed above, in one embodiment, at least one of first and second driven gears 180A, 180B is coupled to a transmission mechanism (not shown) that transmits the rotation of first driven gear 180A and/or of second driven gear 180B to another part of adjustable prosthetic anatomical device 10 for rotation therewith, which accomplishes the adjustment to the size and/or shape of the device. In this way, adjustment assembly 20 can be used to adjust the size and/or shape of an adjustable annuloplasty ring. In a preferred embodiment, this adjustment to the size and/or shape of an adjustable annuloplasty ring is performed in situ, i.e., after the adjustable annuloplasty ring is implanted in a patient (not shown), which can facilitate a more reliable and accurate fit between the particular annuloplasty ring size and/or shape required by the individual patient and the size and/or shape of the adjustable annuloplasty ring. However, in other embodiments, it is also possible to adjust the size and/or shape of an adjustable annuloplasty ring prior to or during the implantation thereof into the patient, in addition to or instead of adjusting the size and/or shape in situ.

In addition to adjustable annuloplasty rings for replacing a mitral valve, the present adjustment assembly is not intended to be so limited, and is also suitable for use in various other prosthetic anatomical devices for use in other types of heart valves, blood vessels, other anatomic orifices, lumens, or openings. For example, an adjustment assembly as described herein could be implemented in gastrointestinal surgery, such as in an adjustable prosthetic device for adjusting the size of a gastroesophageal junction to relieve gastric reflux into a patient's esophagus. Further examples of suitable uses for the present adjustment assembly include, without limitation, implementation in adjustable prosthetic devices for urinary or anal incontinence, anastomotic or ductal strictures, arterial stenosis, cervical incompetence, and/or treatment of morbid obesity. One skilled in the art will also appreciate that other appropriate uses of such an adjustment assembly are also possible.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An adjustment assembly for an adjustable prosthetic valve device, comprising:
    a first gearbox sleeve and a second gearbox sleeve, each gearbox sleeve forming an internal cavity therein, the first and second gearbox sleeves each having at least one opening adjacent a first end thereof;
    a gearbox housing comprising a first gearbox shell and a second gearbox shell adapted to at least partially interlock with one another,
        wherein the first and second gearbox shells each comprise a center portion having an opening therein, each gearbox shell having a first lateral portion and a second lateral portion, wherein at least one of the first and second lateral portions of each gearbox shell has a projection on an exterior surface thereof, each projection adapted to engage a respective opening formed adjacent the first end of one of the gearbox sleeves when the first and second lateral portions are at least partially inserted within the internal cavities of the first and second gearbox sleeves, whereby the first and second gearbox shells are prevented from separating from one another;
    a center gear arranged at least partially within the gearbox housing, the center gear comprising a gear portion and a shaft portion, the shaft portion being adapted to engage an adjustment tool inserted through one of the openings in the gearbox housing; and
    a first driven gear and a second driven gear each arranged at least partially within the gearbox housing, the first and second driven gears each comprising a gear portion that engages the gear portion of the center gear, and a shaft portion;
    wherein the shaft portion of the first driven gear extends at least partially within an opening formed by the first lateral portions of the gearbox shells and the shaft portion of the second driven gear extends at least partially within an opening formed by the second lateral portions of the gearbox shells.

2. The adjustment assembly according to claim 1, wherein at least one of the first gearbox sleeve and the second gearbox sleeve is integrally molded.

3. The adjustment assembly according to claim 1, wherein the gear portion of the center gear and the shaft portion of the center gear are integrally molded with one another.

4. The adjustment assembly according to claim 1, wherein the gear portion and the shaft portion of at least one of the driven gears are integrally molded with one another.

5. The adjustment assembly according to claim 1, wherein the center gear includes a set of internal threads along at least part of a length of a bore formed therein.

6. The adjustment assembly according to claim 1, wherein the center gear includes a hole having a shape adapted to engage an adjustment mechanism of an adjustment tool.

7. An adjustment assembly for an adjustable prosthetic valve device, comprising:
    a first gearbox sleeve having a first end and a second end, and forming a cavity therein;
    a second gearbox sleeve having a first end and a second end, and forming a cavity therein;
    a gearbox housing comprising a first gearbox shell and a second gearbox shell, the first and second gearbox shells each comprising a center portion and two lateral portions extending from opposite sides of the center portion, at least one of the lateral portions of each gearbox shell having a projection on an exterior surface thereof;
    wherein a first end of each gearbox sleeve includes at least one opening adapted to engage a corresponding projection formed on one of the gearbox shells, whereby the gearbox shells are held together to form a gearbox housing;
    wherein the gearbox housing is adapted to support a gear assembly therein, the gear assembly comprising a center gear and two driven gears, each of the gears comprising a shaft portion and a gear portion;
    wherein the gear portion of the center gear engages the gear portions of each of the driven gears;
    wherein an interior surface of each lateral portion of the gearbox shells provides a bearing surface for the shaft portion of a corresponding one of the driven gears; and
    wherein the center portion of each gearbox shell includes an opening adapted to accommodate an end of the shaft portion of the center gear.

8. The adjustment assembly according to claim 7, wherein at least one of the first gearbox sleeve and the second gearbox sleeve is integrally molded.

9. The adjustment assembly according to claim 7, wherein the shaft portion of the center gear and the gear portion of the center gear are integrally molded with one another.

10. The adjustment assembly according to claim 7, wherein the shaft portion and the gear portion of at least one of the driven gears are integrally molded with one another.

11. The adjustment assembly according to claim 7, wherein the center gear includes a set of internal threads along at least part of a length of a bore formed therein.

12. The adjustment assembly according to claim 7, wherein the center gear includes a hole having a shape adapted to engage an adjustment mechanism of an adjustment tool.

13. A gearbox sleeve for an adjustable prosthetic valve device, comprising:
    a first end forming an internal cavity therein;
    a second end adapted to engage a spar of the adjustable prosthetic valve device; and
    at least one opening formed adjacent the first end;
    wherein the internal cavity is adapted for accommodating portions of at least two gearbox shells therein to hold the at least two gearbox shells together;

wherein the at least one opening is adapted to engage a projection formed on an exterior surface of at least one gearbox shell.

14. The gearbox sleeve according to claim 13,
wherein the gearbox sleeve is integrally molded from a single piece of material.

15. A gearbox for an adjustable prosthetic valve device, comprising:
a gearbox housing comprising a first gearbox shell and a second gearbox shell adapted to at least partially interlock with one another,
wherein the first and second gearbox shells each comprise a center portion having an opening therein, each gearbox shell having a first lateral portion and a second lateral portion, at least one of the first lateral portion and the second lateral portion of each gearbox shell having a projection on an exterior surface thereof;
a center gear arranged at least partially within the gearbox housing, the center gear comprising a gear portion and a shaft portion, the shaft portion adapted to engage an adjustment tool inserted through one of the openings in the gearbox housing; and
a first driven gear and a second driven gear each arranged at least partially within the gearbox housing, the first and second driven gears each comprising a gear portion that engages the gear portion of the center gear and a shaft portion;
wherein the shaft portion of the first driven gear extends at least partially within an opening formed by the first lateral portions of the gearbox shells and the shaft portion of the second driven gear extends at least partially within an opening formed by the second lateral portions of the gearbox shells.

16. The gearbox according to claim 15,
wherein the gear portion of the center gear and the shaft portion of the center gear are integrally molded with one another.

17. The gearbox according to claim 15,
wherein the gear portion and the shaft portion of at least one of the driven gears are integrally molded with one another.

18. The gearbox according to claim 15,
wherein the center gear includes a set of internal threads along at least part of a length of a bore formed therein.

19. The gearbox according to claim 15,
wherein the center gear includes a hole having a shape adapted to engage an adjustment mechanism of an adjustment tool.

20. A housing for an adjustment assembly for an adjustable prosthetic valve device, comprising:
a first gearbox sleeve and a second gearbox sleeve, each gearbox sleeve forming an internal cavity therein, the first and second gearbox sleeves each having at least one opening adjacent a first end thereof;
a gearbox housing comprising a first gearbox shell and a second gearbox shell adapted to at least partially interlock with one another,
wherein the first and second gearbox shells each comprise a center portion having an opening therein, each gearbox shell having a first lateral portion and a second lateral portion, wherein at least one of the first and second lateral portions of each gearbox shell has a projection on an exterior surface thereof, each projection adapted to engage a respective opening formed adjacent the first end of one of the gearbox sleeves when the first and second lateral portions are at least partially inserted within the internal cavities of the first and second gearbox sleeves, whereby the first and second gearbox shells are prevented from separating from one another.

21. The housing according to claim 20,
wherein at least one of the first gearbox sleeve and the second gearbox sleeve is integrally molded.

22. The adjustment assembly according to claim 20,
wherein the gear portion of the center gear and the shaft portion of the center gear are integrally molded with one another.

23. An adjustment assembly for an adjustable prosthetic valve device, comprising:
a first gearbox sleeve having a first end and a second end, and forming a cavity therein;
a second gearbox sleeve having a first end and a second end, and forming a cavity therein;
a gearbox housing comprising a first gearbox shell and a second gearbox shell, the first and second gearbox shells each comprising a center portion and two lateral portions extending from opposite sides of the center portion, at least one of the lateral portions of each gearbox shell having a projection on an exterior surface thereof;
wherein a first end of each gearbox sleeve includes at least one opening adapted to engage a corresponding projection formed on one of the gearbox shells, whereby the gearbox shells are held together to form a gearbox housing;
wherein the gearbox housing is adapted to support a gear assembly therein, the gear assembly comprising a center gear and two driven gears, each of the gears comprising a shaft portion and a gear portion;
wherein the gear portion of the center gear engages the gear portions of each of the driven gears;
wherein an interior surface of each lateral portion of the gearbox shells provides a bearing surface for the shaft portion of a corresponding one of the driven gears; and
wherein the center portion of each gearbox shell includes an opening adapted to accommodate an end of the shaft portion of the center gear;
wherein at least one of the first gearbox sleeve and the second gearbox sleeve is integrally molded;
wherein the shaft portion of the center gear and the gear portion of the center gear are integrally molded with one another;
wherein the shaft portion and the gear portion of at least one of the driven gears are integrally molded with one another;
wherein the center gear includes a set of internal threads along at least part of a length of a bore formed therein;
wherein the center gear includes a hole having a shape adapted to engage an adjustment mechanism of an adjustment tool.

* * * * *